United States Patent
Liu et al.

(10) Patent No.: US 10,308,919 B2
(45) Date of Patent: Jun. 4, 2019

(54) METHOD FOR PREPARING ASCORBIC ACID-2-PHOSPHATE USING A RECOMBINANT STRAIN

(71) Applicant: Jiangnan University, Wuxi, Jiangsu (CN)

(72) Inventors: Liming Liu, Jiangsu (CN); Wei Song, Jiangsu (CN); Jing Wu, Jiangsu (CN); Kai Zheng, Jiangsu (CN); Xiulai Chen, Jiangsu (CN)

(73) Assignee: JIANGNAN UNIVERSITY, Wuxi (CN)

(*) Notice: Subject to any disclaimer, the term of this patent is extended or adjusted under 35 U.S.C. 154(b) by 44 days.

(21) Appl. No.: 15/386,588

(22) Filed: Dec. 21, 2016

(65) Prior Publication Data
US 2018/0057802 A1    Mar. 1, 2018

(30) Foreign Application Priority Data

Aug. 31, 2016  (CN) .......................... 2016 1 0793043

(51) Int. Cl.
| | |
|---|---|
| C12P 17/04 | (2006.01) |
| C12N 9/16 | (2006.01) |
| C12N 15/70 | (2006.01) |

(52) U.S. Cl.
CPC .............. *C12N 9/16* (2013.01); *C12N 15/70* (2013.01); *C12P 17/04* (2013.01); *C12Y 301/03002* (2013.01)

(58) Field of Classification Search
None
See application file for complete search history.

(56) References Cited

U.S. PATENT DOCUMENTS

| | | | | |
|---|---|---|---|---|
| 5,250,425 A | * | 10/1993 | Fujio ........................ | C12N 9/12 435/131 |
| 5,578,471 A | * | 11/1996 | Fujio ........................ | C12P 17/04 435/131 |
| 2007/0020624 A1 | * | 1/2007 | Rubenfield ............ | C07K 14/21 435/6.15 |
| 2007/0202566 A1 | * | 8/2007 | Bornscheuer ............ | A23C 9/20 435/69.1 |
| 2009/0297495 A1 | * | 12/2009 | Kerovuo .................. | C11C 1/045 424/94.6 |

(Continued)

OTHER PUBLICATIONS

UniProt Accession No. A0A0D6FFE3_PSEAI, published Mary 27, 2015.*
GenEmbl Accession No. AE004091, published Jan. 31, 2014.*

*Primary Examiner* — Richard C Ekstrom
(74) *Attorney, Agent, or Firm* — SZDC Law P.C.

(57) ABSTRACT

The present invention provides a recombinant strain, construction method thereof and a method for producing acid phosphatase using the recombinant strain. In the invention, the phosphatase gene is obtained from *Pseudomonas aeruginosa* by a molecular biology method, the constructed expression plasmid is transformed into *E. coli* BL21 (DE3). The purified enzyme and whole cells were used for the conversion of ascorbic acid to ascorbic acid-2-phosphate. Ascorbic acid-2-phosphate can be efficiently produced by controlling the ratio of substrates. When the conversion reaction is performed at pH 4.5 under 40° C. for 8 h, the output of ascorbic acid-2-phosphate reaches 54.8 g/L, the conversion is 42.9% and the space time yield is 6.9 g/L/h.

9 Claims, 4 Drawing Sheets

Specification includes a Sequence Listing.

(56) References Cited

U.S. PATENT DOCUMENTS

2010/0159065 A1* 6/2010 Lim ................. C12N 9/16
　　　　　　　　　　　　　　　　　　　　426/2
2014/0044835 A1* 2/2014 Haefner ............ C12N 9/16
　　　　　　　　　　　　　　　　　　　　426/61
2018/0057802 A1* 3/2018 Liu .................. C12N 9/16

* cited by examiner

METHOD FOR PREPARING ASCORBIC ACID-2-PHOSPHATE USING A RECOMBINANT STRAIN

This application claims priority to Chinese Patent Application No.: 201610793043.9, filed on Aug. 31, 2016, which is incorporated by reference for all purposes as if fully set forth herein.

FIELD OF THE INVENTION

The present invention relates to the field of bioengineering, and more particularly to a recombinant strain for producing acid phosphatase, construction method thereof, and a method for preparing ascorbic acid-2-phosphate using the recombinant bacteria.

DESCRIPTION OF THE RELATED ART

Ascorbic acid (AsA, vitamin C) is one of the functional nutrition additives for the creature, which improves the anti-stress ability, enhances immunity, promotes skeletal development, and increases breeding rate. It is widely used, for example, in medicines, foodstuffs, and cosmetics. However, it has the disadvantage of being susceptible to decomposition, such as exposure to heat, air or light. Therefore, steps to maintain the stability of AsA are crucial for AsA application.

The high activity of AsA attributes to the hydroxyl groups in its enol form, esterifying of the hydroxyl group could largely improves its stability to heat, light, acid or oxygen. Commonly organic acids used in the esterification include sulfuric acid, palm acid and phosphoric acid, which respectively correspond to derivatives of AsA-2-sulfate, AsA palmitate and AsA-2-phosphate. Many researches have been focused on AsA-2-phosphate since its advantages including high biological value, stable chemical properties, and good solubility. Thus defects of AsA can be overcome and value of AsA products can be significantly improved.

Chemical synthesis or enzymatic catalysis was used for the preparation of AsA-2-P. Chemical synthesis has been already used for industrial production of AsA-2-P, including acylation and group protection. Acylation method is carried out through following steps: a solution containing AsA, water and pyridine is cooled to −10~0° C. under $N_2$ protection, pH is adjusted to 11 using a 10% NaOH solution, then $POCl_3$ is dropped into the solution, meanwhile NaOH is used to maintain the pH between 11 and 12, the resulting solution is stirred for 0.5 h before sucking filtration to remove the $Na_3PO_4$, the pyridine in the filtrate is removed under vacuum distillation, and then methanol is added, precipitate generated in the methanol solution is dried under vacuum at 40~50° C. and then AsA-2-P is harvested. The method of group protection is realized using AsA as an initial material, AsA and acetone are catalyzed by catalyzers, such as 57% hydronic acid, acetyl chloride, stannous chloride, sulfuric acid, fuming sulfuric acid, dry chlorine hydride, or cupric sulfate/sulfuric acid and so on, to synthesize 5, 6-isopropylidene-L-ascorbic acid (IAA), the product is mixed with pyridine-water solution, and then $POCl_3$ is dropped into the solution. After the reaction, impurities and protecting groups are removed, the resulted compounds are reacted with NaOH or $Na_2CO_3$, and AsA-2-P is harvested. However, the inherent disadvantages of above chemical synthesis methods restrict the industrial development for following reasons: (1) undesired by-products such as AsA pyrophosphate or double AsA-2-phosphate are generated; (2) severe environmental pollution caused by plenty of catalyzers or protective agents; (3) low conversion rate, at least 25% AsA couldn't been transformed; (4) insecure process. Thus there is an urgent need of biological process for AsA-2-P production.

Because of lack of gluconolactonase in microorganisms, AsA cannot be directly synthesized by microorganisms. During the past 30 years, researchers focused on microbial enzymatic conversion of AsA-2-P. In 1993, the "AsA phosphorylase" (acid phosphatase, ACP, EC) was discovered for the first time from *Pseudomonas azotocolligans* ATCC12417, this provided the possibility for enzymatic production of AsA-2-P. In 2004, the ACP was found from *Flavobacterium devorans* ATCC 10829, which possessed a better catalytic performance, the $K_m$ value of the enzyme is 6.2 mM, the molecular weight is 29000 KDa, and the specific activity is 9.42 U/mg pure protein, optimum temperature is 45° C., the optimum pH is 4.5. In 2007, enzyme was prepared using *Brevundimonas diminuta* cell, and AsA-2-P production was realized by using AsA and pyrophosphate (PPi) as the substrates, while the yield of AsA-2-P was only 27.5 g/L, this isn't suitable for industrial production.

SUMMARY OF THE INVENTION

In order to solve the above problems, the invention provides a recombinant strain, construction method thereof, and a method for producing ascorbic acid-2-phosphate using the recombinant strain. The recombinant strain can efficiently produce acid phosphatase with high activity, and ascorbic acid-2-phosphate can be efficiently produced under the conversion of the acid phosphatase.

For the above purpose, the invention provides the following technical solution.

In one aspect, the invention provides a recombinant strain for producing acid phosphatase, and the recombinant strain is obtained by overexpressing an encoding gene of acid phosphatase shown in SEQ ID NO. 1 in *Escherichia coli* via a vector.

Preferably, the encoding gene of acid phosphatase is amplified from *Pseudomonas aeruginosa.*

Preferably, the vector is selected from the group consisting of pET28a, pET22b, pET20a.

Preferably, the *Escherichia coli* is *Escherichia coli* BL21 (DE3).

In another aspect, the invention provides a construction method of a recombinant strain for producing acid phosphatase, the construction method comprises the steps of: combining an encoding gene of acid phosphatase shown in SEQ ID NO. 1 with a vector to obtain a constructed vector, and overexpressing the constructed vector in *Escherichia coli*.

Preferably, the encoding gene of acid phosphatase is amplified from *Pseudomonas aeruginosa.*

More preferably, the vector is selected from the group consisting of pET28a, pET22b, pET20a.

In a preferable embodiment, the *Escherichia coli* is *Escherichia coli* BL21 (DE3).

In a more preferable embodiment, the construction method of the recombinant strain comprises: combining the gene shown in SEQ ID NO. 1 with a vector Pet28a, and expressing the phosphatase shown in SEQ ID NO. 2 in *Escherichia coli* BL21 (DE3).

In still other aspect, the invention provides a method for preparing ascorbic acid-2-phosphate using the recombinant strain. The method comprises the step of reacting ascorbic acid with pyrophosphate under the catalytic conversion of the recombinant strain, to obtain the ascorbic acid-2-phosphate.

In an embodiment, the conversion is performed at pH 3-7 under a temperature of 30-50° C. The conversion time preferably is 2-8 h.

In a preferable embodiment, the conversion is performed at pH 4.0, the conversion temperature is 40° C. and the conversion time is 8 h.

In a specific embodiment, the conversion is performed in a shaker, and the rotate speed is 200 rpm.

Preferably, the molar ratio of ascorbic acid and pyrophosphate is (2.5-6):6.

In some embodiments, wet cells of the recombinant strain are used for conversion, and the amount of the wet cells is 60-100 mg/mmol ascorbic acid.

In some embodiments, the acid phosphatase produced by the recombinant strain is used for the conversion, and the mount of the acid phosphatase is 0.5-1 U/mmol ascorbic acid.

In a preferable embodiment, when the recombinant strain is cultured to an OD600 of 0.4-0.6, IPTG is added to induce the expression of the acid phosphatase.

In an embodiment, the acid phosphatase is crude enzyme obtained by breaking up cells of the recombinant strain.

In a preferable embodiment, the acid phosphatase is purified by Ni-NTA agarose by the steps of:

eluting impurities from the acid phosphatase using 0, 10, 20, 30, 40 and 50 mM imidazole respectively;

specifically eluting the target protein using a 500 mM buffer solution of imidazole; and preforming gradient dialysis to obtain the purified acid phosphatase.

In a specific embodiment, the conversion is catalyzed by the purified acid phosphatase, wherein the concentration of ascorbic acid is 100-500 mM, the concentration of pyrophosphate is 200-600 mM.

In a more specific embodiment, 10 μL purified phosphatase (60 U/mL) is added into a 100-500 mM ascorbic acid solution for the conversion, wherein the concentration of pyrophosphate is 600 mM, and the conversion is performed at 40° C. for 8 h.

Preferably, the concentration of ascorbic acid is 500 mM, and the concentration of pyrophosphate is 600 mM.

Preferably, in the invention the pyrophosphate is sodium pyrophosphate.

In still more other aspect, the invention also provides use of the recombinant strain in foods, medicine and chemical engineering.

In a further aspect, the invention provides a method for producing phosphatase using the recombinant strain, wherein when the recombinant strain is cultured to an $OD_{600}$ of 0.4-0.6, IPTG is added to induce the expression of the acid phosphatase.

In a preferable embodiment, the recombinant strain is cultured to an $OD_{600}$ of 0.4-0.6, 0.4 mM of IPTG (final concentration) is added to induce the expression of the acid phosphatase under 25° C. for 12 h.

By means of the above technical solutions, as compared with the prior art the invention has the following advantages:

In the invention the acid phosphatase from *Pseudomonas aeruginosa* is used for catalyzing the ascorbic acid to produce ascorbic acid-2-phosphate, after expressing in *Escherichia coli*, it still presents high activity, and thus can meet the requirements of industrial production. Furthermore, the molar conversion of the substrates can reach 50.8%, it is 84.1% higher than the highest conversion 27.6% of the prior art. In the method of the invention, the yield of ascorbic acid-2-phosphate can reach 54.8 g/L, it is 96.4% higher than the highest yield 27.9 g/L of the prior art. Additionally, the conversion cycle is not more than 8 h, this will greatly improve the production efficiency.

DESCRIPTION OF THE PREFERRED EMBODIMENTS

The invention will be further illustrated in more detail with reference to accompanying drawings. It is noted that, the following embodiments only are intended for purposes of illustration and are not intended to limit the scope of the invention.

Enzyme Activity Assay:

ACP activity is quantified by HPLC. One unit of ACP is defined as the amount of enzyme that catalyzes the formation of 1 μmol AsA-2-P per min at 40° C. and pH4.5.

Sample preparation: the culture broth was centrifuged at 1000 rpm for 2 min and the supernatant was collect for HPLC analysis.

The concentration of AsA-2-P was determined by high performance liquid chromatography (HPLC) equipped with a C18 ODS HYPERSIL column (Agilent 1200; Agilent Technologies, Palo Alto, Calif., USA), an UV detector (model LC-9A; Shimadzu, Kyoto, Japan) at 254 nm, with mobile phase combined buffer A (0.1 M $KH_2PO_4$, pH 3.0) and buffer B (acetonitrile) on 2:1 by volume, elution at 35° C. and a flow rate of 1 mL/min. Space-time yield (g/L/h)=AsA-2-P yield (g/L)/convertion time (h).

Embodiment 1

Construction of Recombinant Strain Containing Phosphatase Gene (1) The *Pseudomonas aeruginosa* ACP gene (SEQ ID NO.1, GenBanK: CP016214.1) was amplified by PCR with primers PaACP-F (SEQ ID NO. 3) and PaACP-R (SEQ ID NO. 4). The PCR cycle comprised: the first step at 94° C. for 3 minutes; 30 cycles of the second step at 94° C. for 30 seconds (denaturation), at 55° C. for 30 seconds (annealing), and at 72° C. for 1 min (elongation), and then at 72° C. for 10 min (elongation). PCR was carried out adding with LAtaq.

(2) The PCR products were cleaved at the restriction enzyme cleavage sites at both of its ends with BamH I and Hind III and then ligated to pET28a using T4 ligase at 16° C. for 10 h.

(3) The resulting pET28a-PaACP was transformed into *E. coli* BL21 (DE3) competent cells, and then incubated for 12 h. The pET28a-PaACP plasmid was extracted and sequence analysed.

(4) The plasmid containing the target gene was sequenced to select the strain with desired gene, i.e., the recombinant strain containing phosphatase gene E. coli BL21-PaACP.

By the similar method, genes from Staphylococcus aureus and Pseudomonas azotocolligans (with the Genbank ID CP010998.1 and E03360.1) were respectively expressed in E. coli BL21 (DE3) according to the appropriate method, and resulting recombinant strain E. coli BL21-SaACP and E. coli BL21-PazACP were harvest.

Embodiment 2

Induction Expression of Recombinant Strain (1) The positive recombinant strain E. coli BL21-PaACP was cultivated in LB inclined medium for 12 h.

(2) A ring of seed culture was incubated in LB culture for 6 h.

Figure 1:
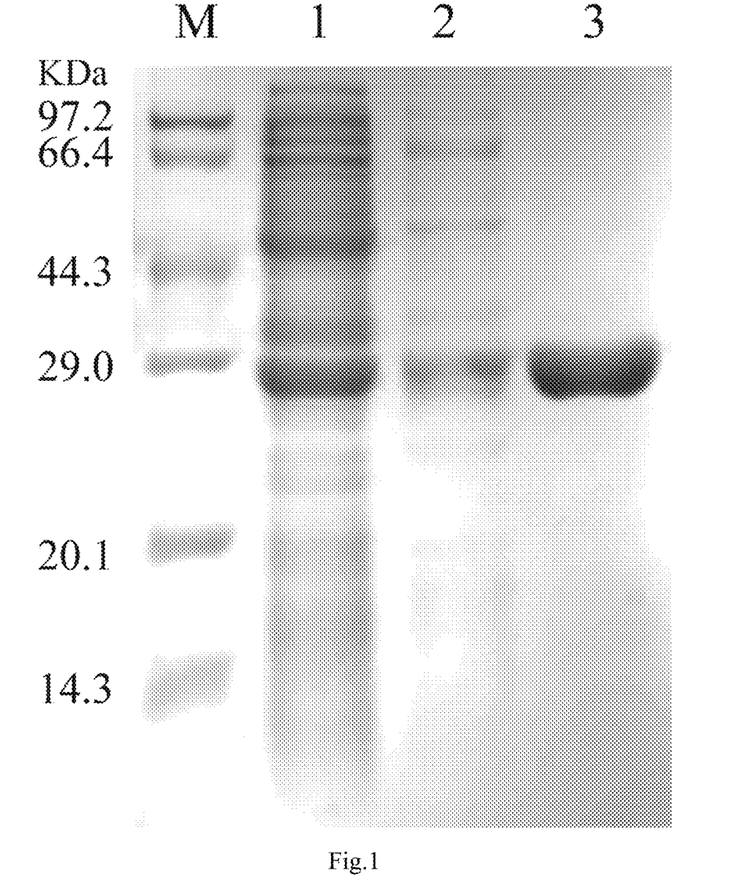
FIG. 1 shows the SDS-PAGE electrophoretogram of expressed proteins, wherein M: marker; 1: non-induced cells; 2: cells induced for 12 h; 3: control cells.

(3) The seed solution of E. coli BL21-PaACP was inoculated in TB fermentation medium, when the optical density at 600 nm ($OD_{600}$) reached 0.6, 0.4 mM IPTG (final concentration) was added, and induction was performed at 25° C. for 12 h, then the strains were collected and washed with sterile saline solution. The culture of recombinant strain without IPTG induction was used as the control. The SDS-PAGE electrophoretogram of protein expression is illustrated in FIG. 1, it can be seen that the phosphatase can be correctly expressed in BL21 strains, and the molecular weight is 29 kDa, and the enzyme activity is 0.3 U/mL.

(4) The E. coli BL21-SaACP and E. coli BL21-PazACP was incubated under same condition, and the resulting phosphatase activity is only 0.18 U/mL and 0.21 U/mL, separately.

Embodiment 3

Purification of Acid Phosphatase

Figure 2:
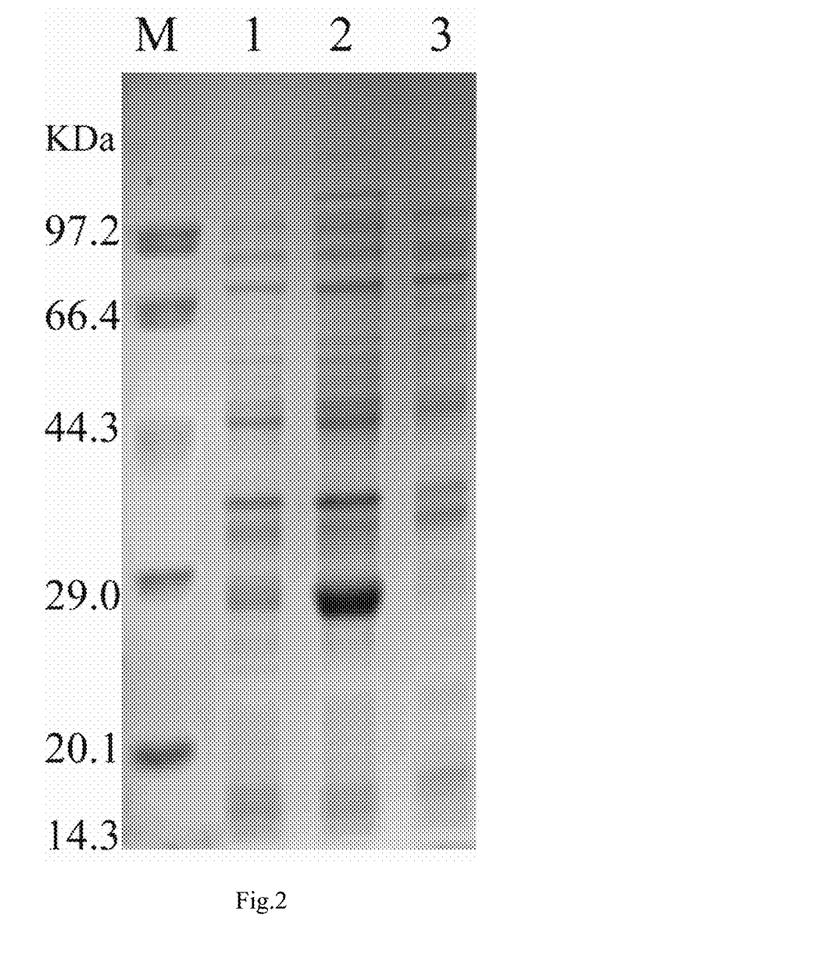
FIG. 2 shows the SDS-PAGE electrophoretogram of proteins, wherein M: marker; 1: crude enzyme; 2: the eluent of protein impurities; 3: the purified enzyme.

The recombinant strain constructed in the embodiment 1 was cultured and induced according to the method of the embodiment 2, the culture broth was centrifuged to harvest the cells; the cells were washed by stroke-physiological saline solution for twice, and then suspended in 50 mM phosphate buffer (pH 7.2), and sonicated by Ultrasonic Cell Disruptor (power 285 W, ultraphonic 4 s, pause 4 s, total 10 min). The resulting solution was centrifuged at 8000× g for 30 min, supernatant filtered by a 0.45 μm filter membrane was the crude enzyme. The crude enzyme was purified by Ni-NTA agarose, and washed with 0, 10, 20, 30, 40 and 50 mM imidazole respectively to remove the impurities, and washed with a 500 mM buffer solution of imidazole to specifically elute the target protein, finally gradient dialysis was performed to obtain the purified acid phosphatase (as shown in FIG. 2). The results of purification was shown in table 1, it can be seen that the specific activity of the purified enzyme produced from E. coli BL21-PaACP strains can reach 14.8 U/mg protein, and the specific activities of the purified enzymes produced from Pseudomonas azotocolligans and Flavobacterium devorans are 6.9 U/mg and 9.4 U/mg protein. Thus, the acid phosphatase of the invention has competitive advantages.

TABLE 1

Purification of Phosphatase

| | Total enzyme activity (U) | Total protein(mg) | Specific activity (U/mg protein) | Purification | Yield (%) |
|---|---|---|---|---|---|
| Crude enzyme | 434.7 | 74.1 | 5.9 | 1 | 100 |
| Purified enzyme | 137.6 | 9.3 | 14.8 | 8 | 31.7 |

Embodiment 4

Production of AsA-2-P by AsA

Figure 3:
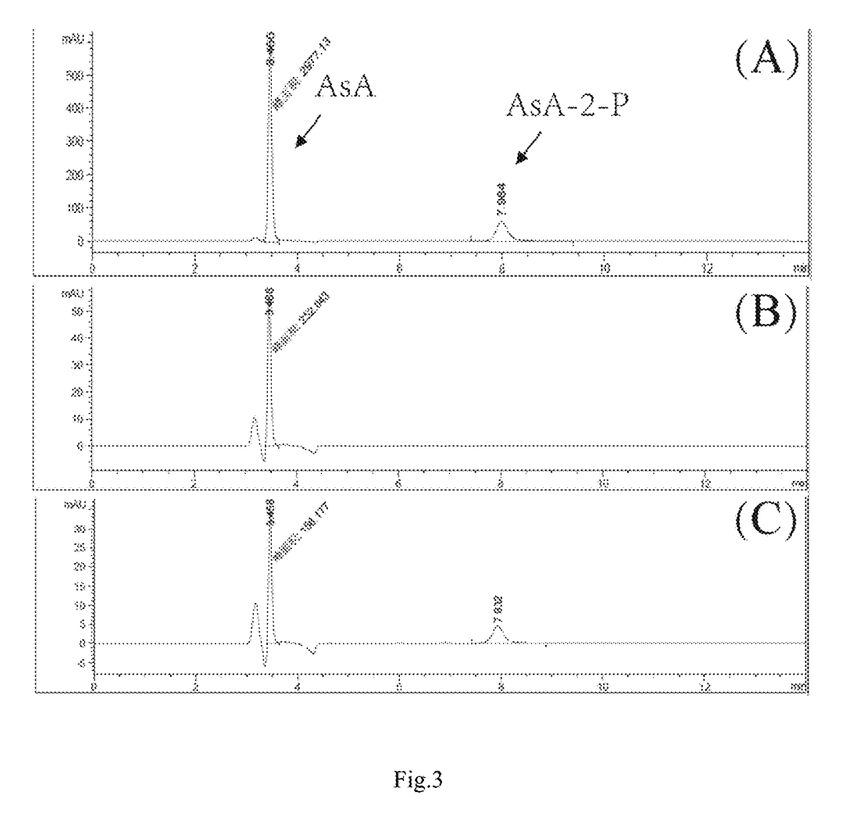
FIG. 3 shows the HPLC chromatogram of converted products, wherein (A): Standard samples of AsA and AsA-2-P, (B): supernatant of the reaction solution (0 h), (C): supernatant of the reaction solution (8 h)

The substrates and purified acid phosphatase were mixed to form a 2 mL reaction system. The reaction mixture included 20 mM phosphate (pH 4.5), 100 mM AsA, 200 mM PPi and 10 μL purified enzyme (60 U/mL) prepared in embodiment 3. After reacting at 40° C. for 8 h, the mixture was filtered through a 0.22 μm filter and analyzed by HPLC. Two prominent peaks corresponding to AsA and AsA-2-P is shown in the HPLC chromatogram (as shown in FIG. 3). It is noted that the output of AsA-2-P reaches 11.8 g/L, the conversion rate was 46.4% and the space time yield was 1.5 g/L/h.

Embodiment 5

Effect of Mole Ratio of AsA to PPi on Production of AsA-2-P

Figure 4:
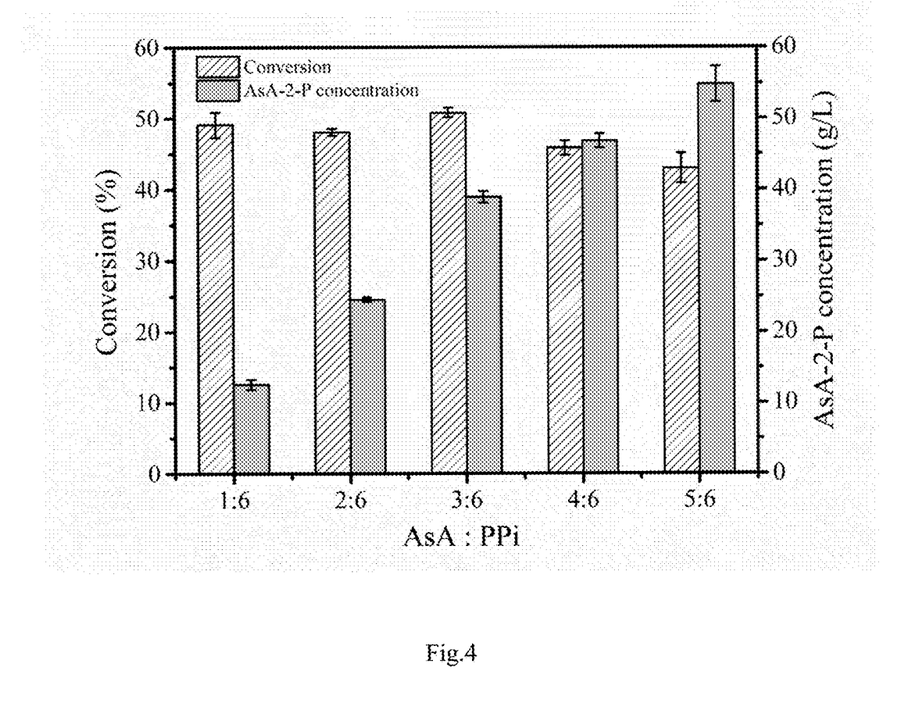
FIG. 4 shows the effect of mole ratio of AsA to PPi on AsA-2-P production.

Utilizing the similar method as the embodiment 4, the concentration of PPi in the reaction mixture was 600 mM, AsA-2-P was produced by different mole ratios of AsA to PPi (1:6, 2:6, 3:6, 4:6, 5:6.). The concentration of AsA-2-P in the supernatant of the reaction solution was determined by HPLC. When the mole ratio of AsA to PPi was 5:6, the concentration of AsA-2-P reached 54.8 g/L, the conversion was 42.9% and the space time yield was 6.9 g/L/h. When the mole ratio of AsA to PPi was 3:6, the highest conversion of AsA-2-P reached 50.8%, the concentration of AsA-2-P was 38.9 g/L and the space time yield was 4.9 g/L/h. While the mole ratio of AsA and PPi was 1:6 and 2:6, the output of AsA-2-P only reached 11.5 g/L and 24.4 g/L respectively. The results is shown in FIG. 4.

Embodiment 6

Production of AsA-2-P by Whole Cell Conversion of AsA

The strains obtained by the embodiment 2 were not purified, and the wet strains were directly used for the whole cell conversion. The concentration of PPi in the reaction mixture was 600 mM, the mole ratio of AsA: PPi was 5:6, and the conversion cycle was 8 h. When the additive amount of strains was 40-50 mg/mmol AsA, the concentration of AsA-2-P was 8.5-23.5 g/L, the conversion was 6.7-18.4% and the space time yield was 1.1-2.9 g/L/h. When the additive amount of strains was 60-100 mg/mmol AsA, the concentration of AsA-2-P reached 32.9-52.7 g/L, the conversion was 25.8-41.3% and the space time yield was 4.1-6.6 g/L/h.

The above preferred embodiments are described for illustration only, and are not intended to limit the scope of the invention. It should be understood, for a person skilled in the art, that various improvements or variations can be made therein without departing from the spirit and scope of the invention, and these improvements or variations should be covered within the protecting scope of the invention.

What is claimed is:

1. A method for preparing ascorbic acid-2-phosphate, comprising:
   providing a recombinant strain for producing an acid phosphatase by overexpressing the acid phosphatase gene shown in SEQ ID NO. 1 in *Escherichia coli* via a vector, wherein the acid phosphatase gene is amplified from *Pseudomonas aeruginosa* and the *Escherichia coli* is *Escherichia coli* BL21 (DE3) and the acid phosphatase has a specific activity of about 14.8 U/mg protein; and
   reacting ascorbic acid with pyrophosphate under the catalytic conversion of the recombinant strain, to obtain the ascorbic acid-2-phosphate,
   wherein the molar ratio of ascorbic acid and pyrophosphate is 4:6.

2. The method as claimed in claim 1, wherein the conversion is performed at pH 3-7 under a temperature of 30-50° C.

3. The method as claimed in claim 1, wherein wet cells of the recombinant strain are used for conversion, and the amount of the wet cells is 60-100 mg/mmol ascorbic acid.

4. The method as claimed in claim 2, wherein wet cells of the recombinant strain are used for conversion, and the amount of the wet cells is 60-100 mg/mmol ascorbic acid.

5. The method as claimed in claim 1, wherein the acid phosphatase produced by the recombinant strain is used for the conversion, and the amount of the acid phosphatase is 0.5-1 U/mmol ascorbic acid.

6. The method as claimed in claim 2, wherein the acid phosphatase produced by the recombinant strain is used for the conversion, and the amount of the acid phosphatase is 0.5-1 U/mmol ascorbic acid.

7. The method as claimed in claim 1, wherein when the recombinant strain is cultured to an $OD_{600}$ of 0.4-0.6, and IPTG is added to induce the expression of the acid phosphatase.

8. The method as claimed in claim 5, wherein the acid phosphatase is purified by Ni-NTA agarose by the steps of: removing impurities from the acid phosphatase by using 0, 10, 20, 30, 40 and 50 mM imidazole; eluting the acid phosphatase by using a 500 mM buffer solution of imidazole; and then performing gradient dialysis to obtain the acid phosphatase.

9. The method as claimed in claim 1, wherein the vector is selected from the group consisting of pET28a, pET22b, and pET20a.

* * * * *

SEQUENCE LISTING

<160> NUMBER OF SEQ ID NOS: 4

<210> SEQ ID NO 1
<211> LENGTH: 726
<212> TYPE: DNA
<213> ORGANISM: Pseudomonas aeruginosa
<220> FEATURE:
<223> OTHER INFORMATION: Pseudomonas aeruginosa ACP gene

<400> SEQUENCE: 1

```
atgaacaaca agaccctatg cccttcgctc ttgctctgcc tttcgctgct tgcaccgctg      60
tcttgtctcg gggagaccgc cgccgcgccc tatccgctgg cccacccacc gcgcctggcc     120
gactacctcc cgccgccgcc ggcggcggac tcggctgcgg ccgtcgccga tctcggcgcg     180
gtgctggagg cgcaacgcct gcacgcgccc gaacaggtac gccgggtacg cgcccacgac     240
cagtgggagg acaacgtctt ccccttcgcc ggcgacctgc tgggcgcctc gttcgacaag     300
gaacgcctgc cgctgacccg gagtttcttc aaccgcgccc aggaaaacct ggtcgaggtg     360
ctgatgccgg cgaagaagca cttcgcccgc ccgcgtccct acgaagtgac accgaaggtg     420
aagccggtgc tgccgccgcc ggaggggggag tcctatccca gcggccacac catggacagc     480
tacttcaagg cctcgctgct gagcatgctg gtgccggagc atcacgatgc gttcttcgcc     540
cgcgccgagg agcatgcgca gagccgtgtg ctggccggcg tgcacttccc cagcgacctg     600
gaaggcgggc agaccgccgc cgcggcgctg gtggcgagcc tgctggccga tccggcggtg     660
gccgccgact cgccgcgggt gcgcgaggag ctgcgcggcg cgctgggggtt gccgaaactc     720 cagtag                                                                726
```

<210> SEQ ID NO 2
<211> LENGTH: 241
<212> TYPE: PRT
<213> ORGANISM: Pseudomonas aeruginosa
<220> FEATURE:
<223> OTHER INFORMATION: Pseudomonas aeruginosa protein expression

<400> SEQUENCE: 2

```
Met Asn Asn Lys Thr Leu Cys Pro Ser Leu Leu Cys Leu Ser Leu
1               5                   10                  15

Leu Ala Pro Leu Ser Cys Leu Gly Glu Thr Ala Ala Ala Pro Tyr Pro
            20                  25                  30

Leu Ala His Pro Pro Arg Leu Ala Asp Tyr Leu Pro Pro Pro Ala
        35                  40                  45

Ala Asp Ser Ala Ala Ala Val Ala Asp Leu Gly Ala Val Leu Glu Ala
    50                  55                  60

Gln Arg Leu Arg Thr Pro Glu Gln Val Arg Arg Val Arg Ala His Asp
65                  70                  75                  80

Gln Trp Glu Asp Asn Val Phe Pro Phe Ala Gly Asp Leu Leu Gly Ala
                85                  90                  95

Ser Phe Asp Lys Glu Arg Leu Pro Leu Thr Arg Ser Phe Phe Asn Arg
            100                 105                 110

Ala Gln Glu Asn Leu Val Glu Val Leu Met Pro Ala Lys Lys His Phe
        115                 120                 125

Ala Arg Pro Arg Pro Tyr Glu Val Thr Pro Lys Val Lys Pro Val Leu
    130                 135                 140

Pro Pro Pro Glu Gly Glu Ser Tyr Pro Ser Gly His Thr Met Asp Ser
145                 150                 155                 160

Tyr Phe Lys Ala Ser Leu Leu Ser Met Leu Val Pro Glu His His Asp
```

-continued

```
                165                 170                 175
Ala Phe Phe Ala Arg Ala Glu Glu His Ala Gln Ser Arg Val Leu Ala
            180                 185                 190

Gly Val His Phe Pro Ser Asp Leu Glu Gly Gly Gln Thr Ala Ala Ala
        195                 200                 205

Ala Leu Val Ala Ser Leu Leu Ala Asp Pro Ala Val Ala Ala Asp Phe
    210                 215                 220

Ala Ala Val Arg Glu Glu Leu Arg Gly Ala Leu Gly Leu Pro Lys Leu
225                 230                 235                 240

Gln

<210> SEQ ID NO 3
<211> LENGTH: 31
<212> TYPE: DNA
<213> ORGANISM: Artificial Sequence
<220> FEATURE:
<223> OTHER INFORMATION: DNA Primer

<400> SEQUENCE: 3
cgcggatccg agaccgccgc gcgccctat c                              31

<210> SEQ ID NO 4
<211> LENGTH: 33
<212> TYPE: DNA
<213> ORGANISM: Artificial Sequence
<220> FEATURE:
<223> OTHER INFORMATION: DNA Primer

<400> SEQUENCE: 4
cccaagcttc tactggagtt tcggcaaccc cag                           33
```